United States Patent
Bambino et al.

(10) Patent No.: US 10,279,090 B2
(45) Date of Patent: May 7, 2019

(54) BREAST MILK STORAGE SYSTEM

(71) Applicant: NUK USA LLC, Tarrytown, NY (US)

(72) Inventors: Michael Bambino, Sunnyside, NY (US); Robert Joachim, Glen Rock, NJ (US); Mario A. Turchi, Tenafly, NJ (US); Ralph W. Dowdell, III, Trenton, NJ (US); Richard Rubin, Fairfield, NJ (US); Allison F. Capozza, West Point, NY (US)

(73) Assignee: NUK USA LLC, Tarrytown, NY (US)

( * ) Notice: Subject to any disclaimer, the term of this patent is extended or adjusted under 35 U.S.C. 154(b) by 990 days.

(21) Appl. No.: 14/680,004

(22) Filed: Apr. 6, 2015

(65) Prior Publication Data
US 2016/0287766 A1 Oct. 6, 2016

(51) Int. Cl.
*A61M 1/06* (2006.01)

(52) U.S. Cl.
CPC .................. *A61M 1/062* (2014.02)

(58) Field of Classification Search
CPC .. A61M 1/06–1/068; A61J 9/00–9/005; B65B 43/54; B65B 39/08; B65D 45/02; B65D 45/025; B65D 45/04; B65D 45/06; B65D 45/22; B65D 45/32; B65D 45/322; B65D 45/325
See application file for complete search history.

(56) References Cited

U.S. PATENT DOCUMENTS

| | | | | |
|---|---|---|---|---|
| 2,042,858 | A * | 6/1936 | Nicolas | B65B 39/08 141/314 |
| 2,100,501 | A * | 11/1937 | Bennett | B65B 39/08 248/101 |
| 5,257,865 | A * | 11/1993 | Tani | B65D 35/12 215/11.3 |
| 5,358,476 | A | 10/1994 | Wilson | |
| 6,050,432 | A | 4/2000 | Koehnke | |
| 6,328,082 | B1 | 12/2001 | Lafond | |
| 6,575,202 | B2 | 6/2003 | Lafond | |
| 6,616,000 | B1 | 9/2003 | Renz | |
| 6,884,229 | B2 | 4/2005 | Renz | |
| 7,004,339 | B2 | 2/2006 | Renz | |
| 7,666,162 | B2 | 2/2010 | Renz et al. | |
| 7,776,008 | B2 | 8/2010 | Renz et al. | |
| 8,357,116 | B2 | 1/2013 | Simdon | |
| 2002/0156419 | A1 | 10/2002 | Silver et al. | |
| 2005/0245861 | A1* | 11/2005 | Dunn | A61J 9/00 604/77 |

(Continued)

*Primary Examiner* — Bhisma Mehta
*Assistant Examiner* — Laura C Schell
(74) *Attorney, Agent, or Firm* — Eversheds Sutherland (US) LLP

(57) ABSTRACT

A breast milk storage system which comprises a mandrel for selective engagement with a bottle connector of a breast pump. The storage system also includes at least one clamp in pivotal engagement with the mandrel, and a lock ring. The lock ring is positioned for rotation about the mandrel and the at least one clamp. Rotation of the lock ring effectuates pivoting of the at least one clamp between an open position and a closed position. In the closed position, the at least one clamp is pivoted with respect to the mandrel and presses against the mandrel so as to retain a storage bag in place by pinching said storage bag between the at least one clamp and the mandrel.

16 Claims, 8 Drawing Sheets

(56) References Cited

U.S. PATENT DOCUMENTS

| | | |
|---|---|---|
| 2006/0074379 A1 | 4/2006 | Hunt |
| 2009/0088684 A1 | 4/2009 | Rohrig |
| 2010/0292636 A1 | 11/2010 | Renz et al. |
| 2013/0110037 A1 | 5/2013 | Simdon |
| 2014/0107608 A1 | 4/2014 | McBean et al. |
| 2014/0213964 A1 | 7/2014 | Taheri |
| 2014/0343486 A1 | 11/2014 | Taheri |

* cited by examiner

BREAST MILK STORAGE SYSTEM

FIELD OF THE INVENTION

The present invention relates to a breast milk storage system, and, more particularly, to storage system which engages with existing breast milk pumps to deposit expressed breast milk directly into a plastic storage bag.

BACKGROUND OF THE INVENTION

Conventional breast pumps are typically designed to engage with a bottle. The bottle will often screw into the bottom of the breast pump, and expressed breast milk is pumped directly from the breast, through the breast shield of the breast pump, and into the bottle. However, such bottles are not commonly used for long term storage of the breast milk. Rather, breast milk is usually poured from the bottle into a more long-term storage container—typically, a plastic freezer bag specifically designed for breast milk storage. The bag of milk is then frozen for future use. However, this process can be cumbersome and messy, and can often result in the loss of some breast milk from spillage during the transfer process between bottle and storage bag. Additionally, the bottle itself requires cleaning, which adds an extra step to the entire process.

Existing prior art systems have tried to do away with the need for the bottle by pumping breast milk directly into a storage bag. However, such prior art systems suffer from various flaws, including unstable attachment points, incompatibility with various models of breast pumps, likelihood for spillage, etc.

BRIEF SUMMARY OF THE INVENTION

The present invention relates to a breast milk storage system that comprises a mandrel for selective engagement with a bottle connector of a breast pump or shield for a breast pump. The storage system also includes at least one clamp (referred to hereinafter as "clamps" for ease of reference) in pivotal engagement with the mandrel, and a lock ring. The lock ring may be positioned for rotation about the mandrel and the clamps. Rotation of the lock ring effectuates pivoting of the clamps between an open position and a closed position. In the closed position, the clamps are pivoted with respect to the mandrel and press against the mandrel so as to retain a storage bag in place by pinching the storage bag between the clamps and the mandrel.

Each of the clamps may include at least one tooth extending inwardly therefrom. The mandrel may include at least one recess corresponding to at least one tooth from each clamp. When the clamps are in the closed position, the tooth/teeth engage with the recess/recesses to pinch the storage bag in place. The lock ring may include at least one cam for forcing the clamps into their closed position upon rotation of the lock ring.

The mandrel may include an engagement portion for selective engagement with the bottle connector of the breast pump or shield, as well as a spout from which breast milk may exit the mandrel. The mandrel may also include a body extending from the engagement portion to the spout. The body may further include a flow passageway to allow breast milk to flow from the bottle connector to the spout. In some embodiments, the engagement portion of the mandrel may not fit with the bottle connector of a specific breast pump. Thus, the breast milk storage system may also include an adaptor for allowing engagement of the engagement portion of the mandrel with the bottle connector of the breast pump or shield. Hereinafter, the breast pump and shield will, individually or collectively, be referred to as a breast pump.

Other aspects and advantages of the present invention will be apparent from the following detailed description of the preferred embodiments and the accompanying drawing figures.

Figure 1:
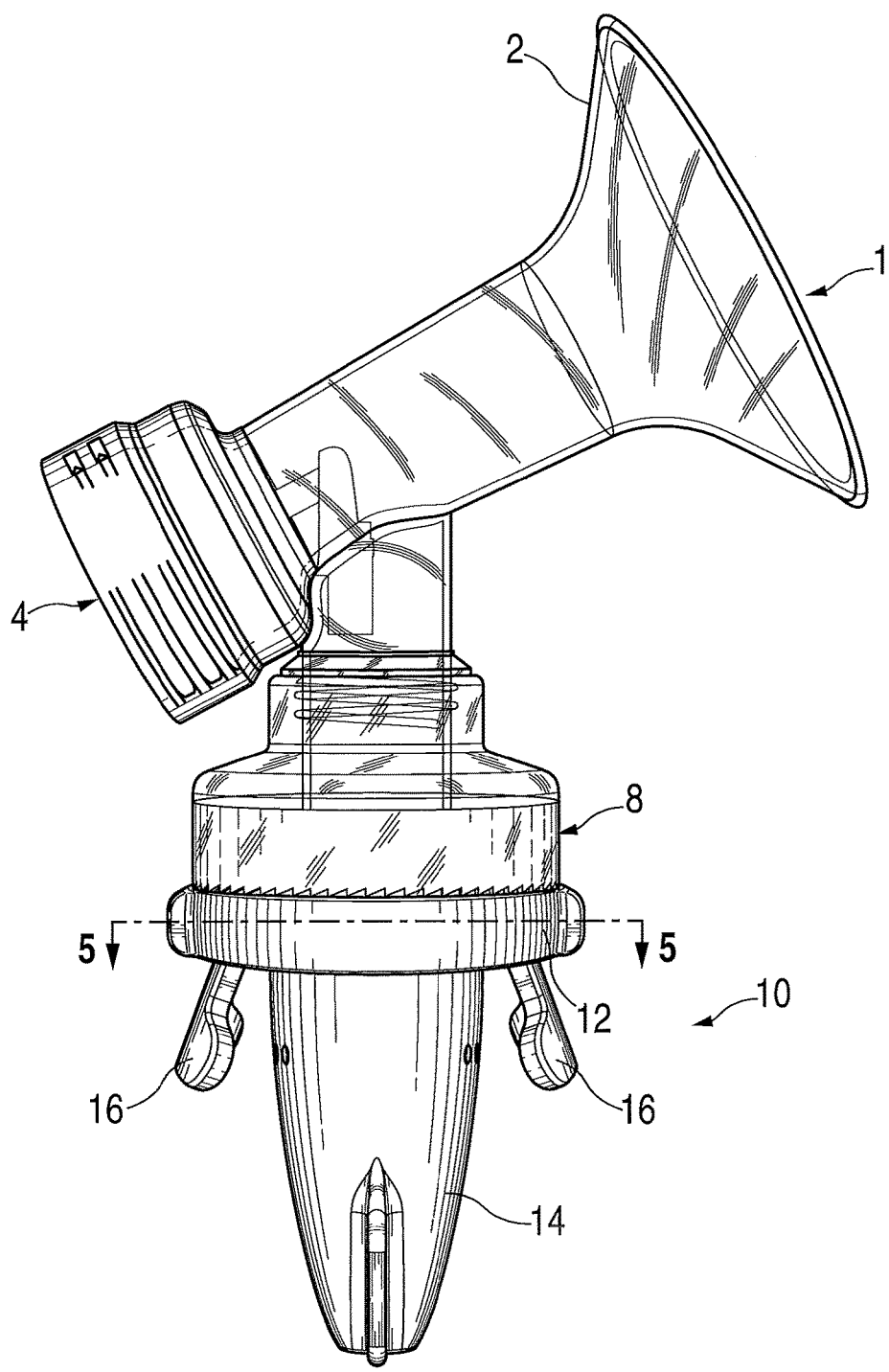
FIG. 1 is a side elevation view of a storage system in its open position, as engaged with a prior art breast pump.

While the disclosure is susceptible to various modifications and alternative forms, a specific embodiment thereof is shown by way of example in the drawings and will herein be described in detail. It should be understood, however, that the drawings and detailed description presented herein are not intended to limit the disclosure to the particular embodiment disclosed, but to the contrary, the intention is to cover all modifications, equivalents, and alternatives falling within the spirit and scope of the present disclosure as defined by the appended claims.

DETAILED DESCRIPTION OF THE INVENTION

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

Figure 2:
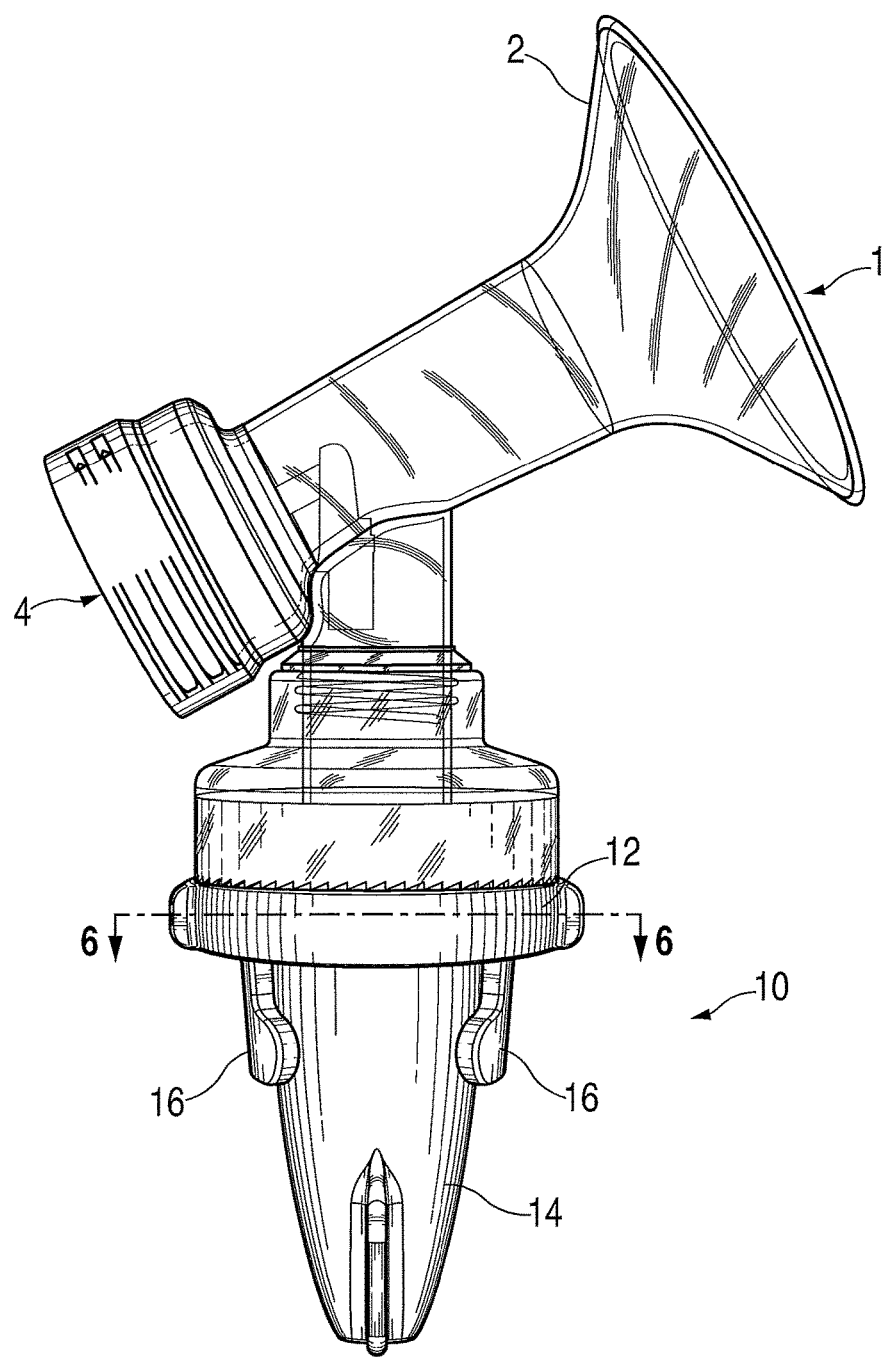
FIG. 2 is a side elevation view of the storage system of FIG. 1 in its closed position, as engaged with a prior art breast pump.

Referring to the drawings particularly by reference numbers wherein like numerals refer to like parts, FIGS. 1 and 2 illustrate components of a prior art breast pump 1, including a breast shield 2 and a pump connector 4. As would be understood, the pump connector 4 of breast pump 1 would connect via a hose or tube (not shown) with a pumping mechanism (not shown) to effectuate the expression of breast milk through the breast shield 2. Once received through the breast shield 2, expressed milk typically passes downwardly through bottle connector 8 and into a bottle (not shown). Depending on the brand and model of breast pump 1, bottle connector 8 may have various shapes and sizes. Most bottle connectors 8 include threads to allow a similarly threaded bottle to be screwed on. However, prior art bottle connectors 8 may use other mechanisms for selective securement with a bottle, as would be understood in the art.

In both FIGS. 1 and 2, an embodiment of a storage system 10 is releasably engaged with the bottle connector 8 of the prior art breast pump 1 in place of a bottle. As shown, the storage system 10 includes a locking ring 12, a mandrel 14, and opposing clamps 16. In FIG. 1, the opposing clamps 16 are shown in an "open" position. When the clamps 16 are in their open position, a storage bag may be placed around the mandrel 14 for filling, or removed from the mandrel 14 for long term storage. In FIG. 2, the opposing clamps 16 are shown in a "closed" position, having pivoted into engagement with the mandrel 14 due to rotation of the locking ring 12. When the clamps 16 are in their closed position, a storage bag which was previously placed around the mandrel 14 is secured in place between the clamps 16 and the mandrel 14 for filling.

Figure 3A:
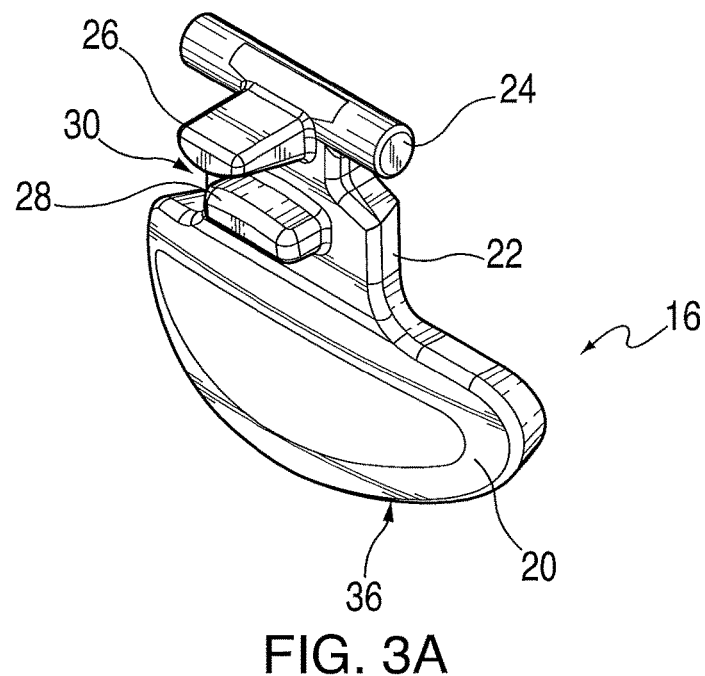
FIG. 3A is a top perspective view of the clamp from the storage system of FIG. 1.
Figure 3B:
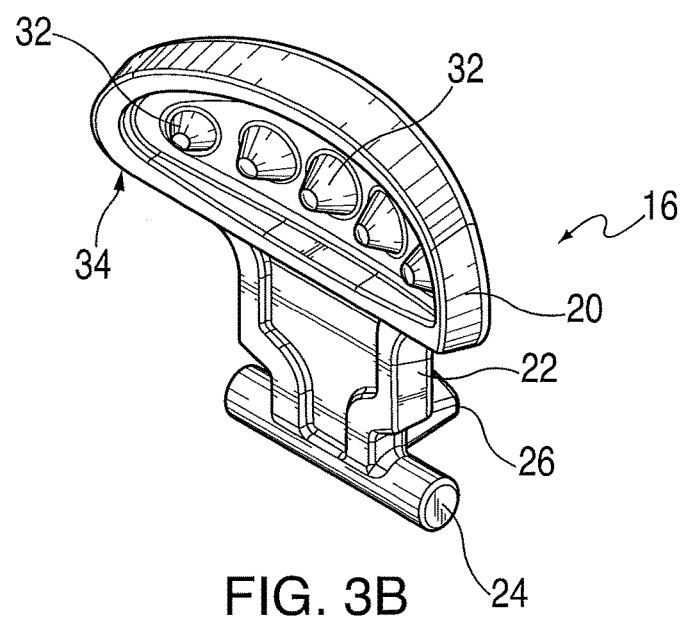
FIG. 3B is a bottom perspective view of the clamp of FIG. 3A.

FIGS. 3A and 3B illustrate an embodiment of a clamp 16 in additional detail. Each clamp 16 may include a paddle 20. Paddle 20 may be wider than a neck portion 22. Neck portion 22 may extend from the paddle 20 to an axle 24. When a clamp 16 moves from its open position to its closed position or vice versa, the clamp pivots about the axle 24. As best seen in FIG. 3A, each clamp may also include an upper flange 26 and a lower flange 28 which define a gap 30 there between. As will be discussed in detail below, gap 30 may be sized, shaped, and positioned to receive at least a part of lock ring 12 between the upper and lower flanges 26, 28. However, upper and lower flanges 26, 28 may take a different form or be removed completely, depending on the corresponding structure of lock ring 12, as will be discussed below. Additionally, as can best be seen in FIG. 3B, the paddle 20 of each clamp may include at least one tooth 32 on an inside face 34 thereof (as compared to outer face 36, which is visible in FIG. 3A). A tooth 32 may also be referred to as a protrusion 32, or spike 32, or the like. Instead of or in addition to one or more teeth 32, a clamp 16 may include one or more ribs (not shown).

Figure 4A:
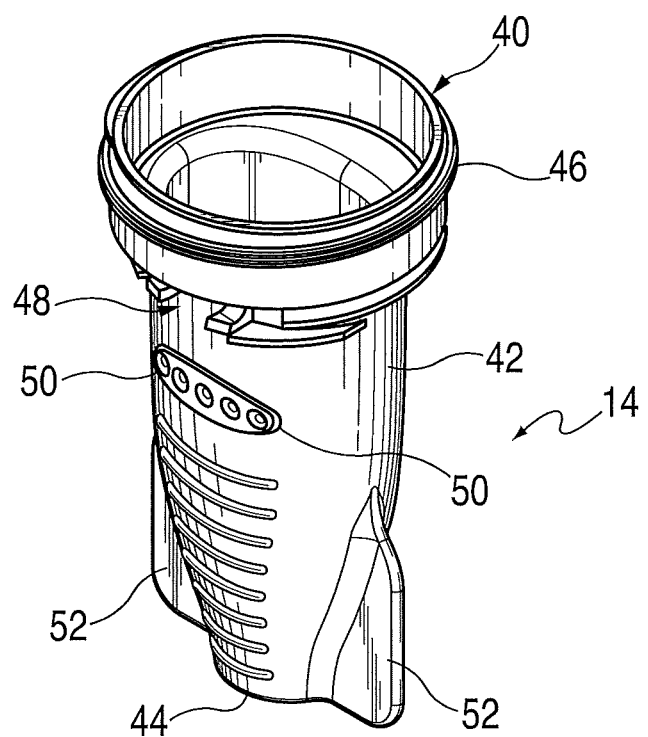
FIG. 4A is top perspective view of the mandrel from the storage system of FIG. 1.
Figure 4B:
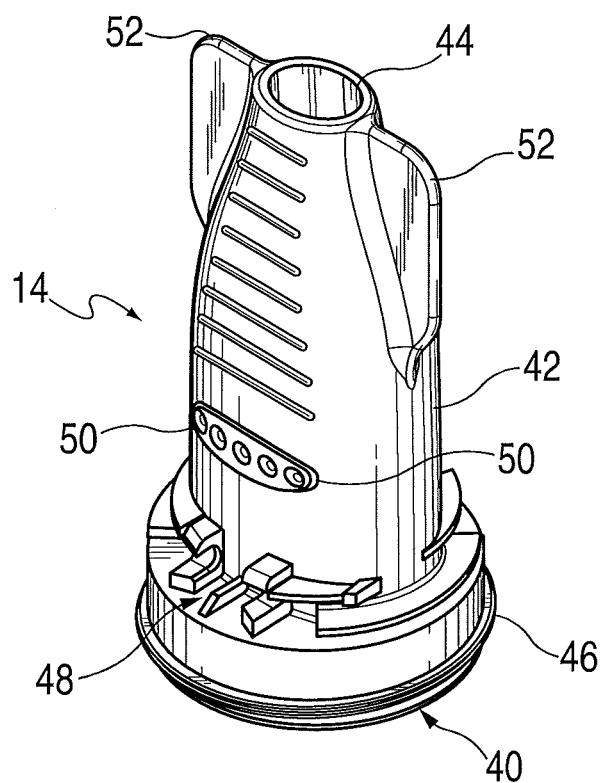
FIG. 4B is bottom perspective view of the mandrel from FIG. 4A.

FIGS. 4A and 4B illustrate an embodiment of a mandrel 14 in additional detail. A mandrel 14 may include an engagement portion 40, a body 42, and a spout 44. As shown, the body 42 is generally hollow and extends from the engagement portion 40 to the spout 44. It is noted that body 42 need not be hollow. Instead, body 42 may include one or more flow passageways for milk to pass from the engagement portion 40, through the body 42, to the spout 44, and from the spout 44 out of the mandrel 14 and into a storage bag (not shown). In this regard, the hollow body 42 itself may be considered a flow passageway.

In operation, the engagement portion 40 of mandrel 14 may engage with the bottle connector 8 of a prior art breast pump 1. As shown mandrel 14 includes one or more threads 46 around the engagement portion 40, for screwing the mandrel 14 (and thus the storage system 10) into the bottle connector 8 of a prior art breast pump 1. However, as noted above, various prior art breast pumps 1 may have differently sized, shaped, and structured bottle connectors 8. Thus, an adaptor (not shown) may be used between the engagement portion 40 and a bottle connector 8. As would be understood in the art, an adaptor would include a first end which is designed to mate with the threads 46 of engagement portion 40, and a second end which is structured to mate with the bottle connector 8 of a prior art breast pump 1. The storage system 10 may be sold as a kit with one or more such adaptors. For the purposes hereof, the engagement portion 40 and threads 46 of mandrel 14 will be discussed as mating directly with a bottle connector 8. However, it should be recognized that an adaptor could be positioned there between.

As shown in FIGS. 4A and 4B, the body 42 of mandrel 14 may generally taper from the wider engagement portion 40 to the narrower spout 44. Although such a narrowing is not vital, it has been found to assist with slipping a storage bag over the mandrel 14, and with the funneling of breast milk through the mandrel 14 and into such a storage bag. Body 42 of mandrel 14 may also include opposing securement points 48. Each securement point 48 may be configured to receive the axle 24 of a clamp 16 to allow pivoting of the clamp 16 about its axle 24. Various structures for a securement point 48 are envisioned, as would be understood in the art. As a non-limiting example, an axle 24 may be snap-fit into a securement point 48 to be retained directly by the securement point 48 for pivotal movement. Alternatively, an axle 24 may simply fit into a securement point 48, and may be retained in place by lock ring 12 fitting there around. Again, other structures may be used which allow a clamp 16 to move from its open position to its closed position, as would be easily understood by a person of ordinary skill in the art.

Positioned generally below each securement point 48 on body 42, mandrel 14 may include at least one recess 50. Preferably, the size, shape, number, and position of recesses 50 corresponds to the size, shape, position, and number of teeth 32 on the corresponding clamp 16. Thus, when a clamp 16 is in its closed position, at least one of the teeth 32 (referred to hereinafter as teeth 32, although it is again noted that there may be only a single tooth 32) of the clamp 16 has pivoted into engagement with recess/recesses 50 (referred to hereinafter as recesses 50, although it is again noted that the number of recesses 50 corresponds to the number of teeth 32). As discussed in detail below, when a storage bag is clamped between teeth 32 and recesses 50, the storage bag is retained in place for filling. Preferably, the storage bag is not punctured by its position between the engagement of teeth 32 and recesses 50, although in other embodiments such puncturing may occur. Mandrel 14 may also include at least one wing 52. Wings 52 may help to guide a storage bag up and over the mandrel 14. In an embodiment in which a clamp 16 includes a rib rather than or in addition to teeth 32, the mandrel 14 may include a corresponding recess 50 sized and shaped to receive such a rib, or may not include a recess 50 corresponding to such a rib. When no corresponding recess 50 is formed in mandrel 14, such a rib may be composed of a soft, compressible material to retain a plastic storage bag against the mandrel 14 via friction.

Figure 5:
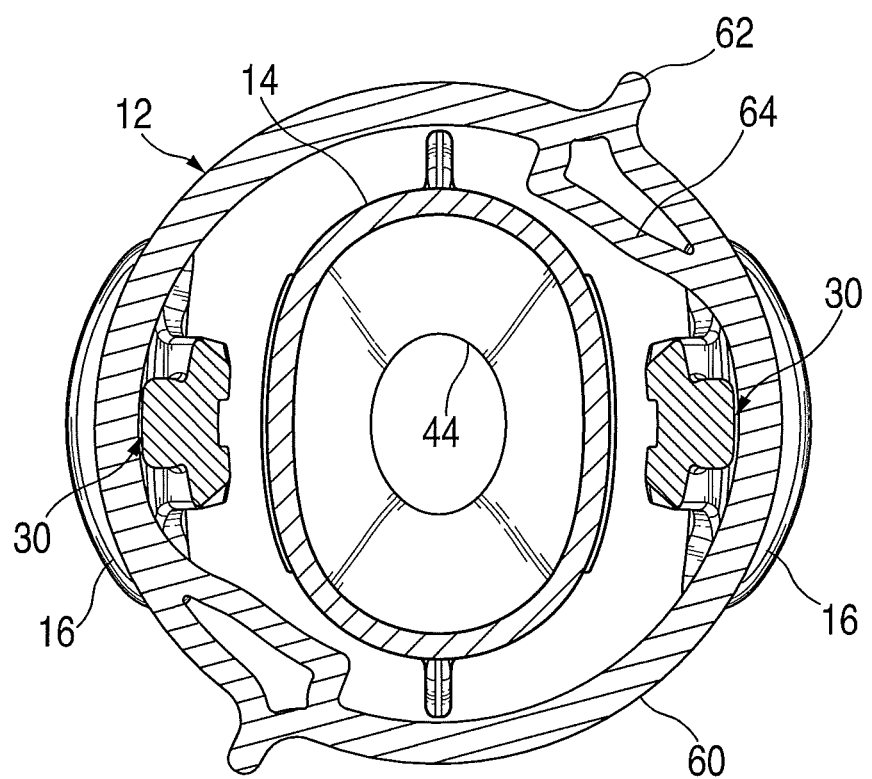
FIG. 5 is a cross-sectional view taken along line 5-5 in FIG. 1.
Figure 6:
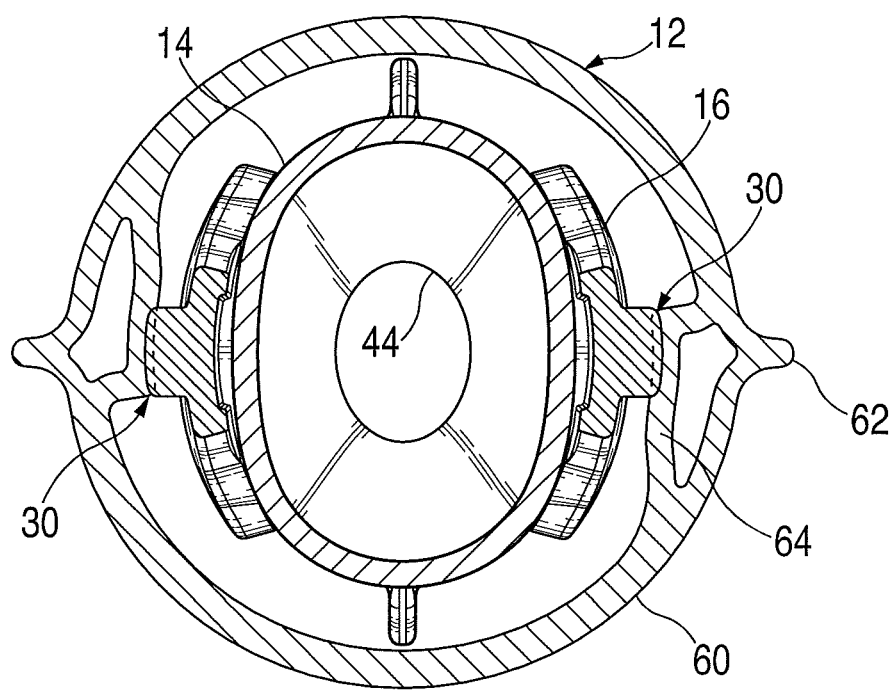
FIG. 6 is a cross-sectional view taken along line 6-6 in FIG. 2.

FIGS. 5 and 6 illustrate cross-sectional views through lock ring 12, mandrel 14, and clamps 16 as taken across lines 5-5 and 6-6 from FIGS. 1 and 2, respectively. Lock ring 12 includes a ring portion 60, at least one flange portion 62, and at least one cam 64. In the embodiment shown in FIGS. 5 and 6, the number of cams 64 corresponds to the number of clamps 16. As can be seen, ring portion 60 of lock ring 12 is positioned around the mandrel 14 and clamps 16 proximate the gap 30 in each clamp 16. Each cam 64, as shown, is embodied generally by a sloping inward extension of ring portion 60.

FIG. 5, illustrates the clamps 16 and lock ring 12 are positioned in the open position. As can be seen, the cams 64 are positioned away from the clamps 16. However, in FIG. 6, the clamps 16 and lock ring 12 are shown in the closed position. Lock ring 12 has been rotated so that the cams 64 have come into engagement with the respective gaps 30 of clamps 16. As cams 64 are generally defined by sloping inward extensions of ring portion 60, the cams have forced clamps 16 to pivot inwardly as discussed above, such that the teeth 32 of the clamps 16 engage with the recesses 50 of the mandrel 14. Counter-rotation of lock ring 12 disengages the cams 16 from the respective gaps 30 in clamps 16, such that clamps 16 may move back into their open positions. As would be understood by a person of ordinary skill in the art, movement of the clamps 16 into their open positions may be caused by a biasing mechanism (not shown), such as a spring. Alternatively, in addition to cams 64 on lock ring 12, another set of generally outwardly extending cams may be included with said lock ring 12, such that all such cams work together as a track for inward and outward rotation of clamps 16. Flanges 62 may assist a user with rotation of the lock ring 12.

Figure 7:
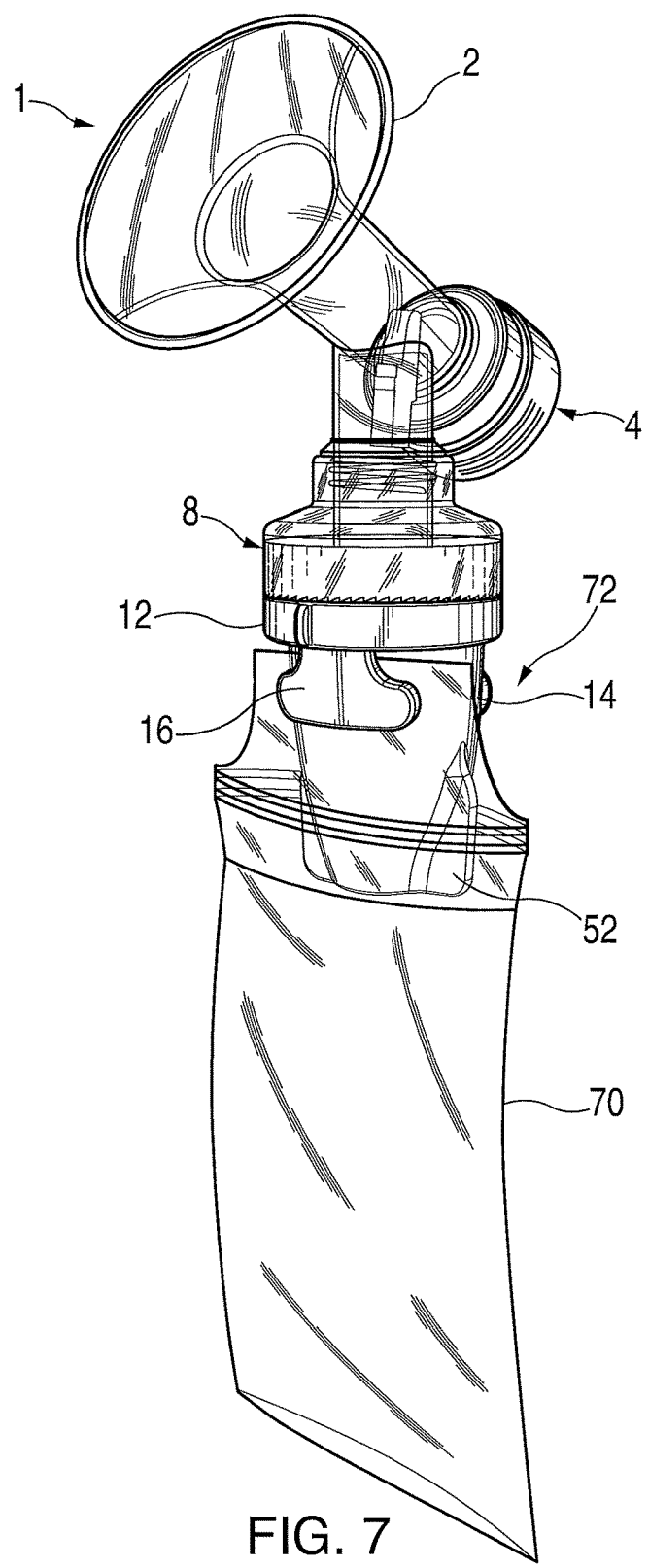
FIG. 7 is a perspective view of the storage system of FIG. 1 retaining a storage bag.

FIG. 7 illustrates an example embodiment of storage system 10 in operation, and engaged with an example storage bag 70. The open end 72 of storage bag 70 has been slipped up over the mandrel 14, as guided by the wings 52. The bag 70 was positioned between the mandrel 14 and the clamps 16 when the clamps 16 were in their open position. The lock ring 12 was rotated, such that clamps pivoted into their closed position. The teeth 32 on the clamps 16 engaged with the recesses 50 in the mandrel 16, thereby pinching the open end 72 of storage bag 70 there between. Thereby, the storage bag 70 is retained in place for filling. As milk is expressed through breast shield 2 and down through bottle connector 8, the milk then passes into the body 42 of mandrel 14, where it is funneled down and out of mandrel 14 through spout 44 and into the storage bag 70. Once the storage bag 70 has been adequately filled, the lock ring 12 is counter-rotated, and the clamps 16 pivot back into their open positions. This allows the user to remove the storage bag 70 from mandrel 14 for sealing and storage.

Thus, there has been shown and described several embodiments of a novel storage system for breast milk. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

The invention claimed is:

1. A breast milk storage system comprising:
   a mandrel for selective engagement with a bottle connector of a breast pump, the mandrel comprising a body comprising:
      an engagement portion end defining a first opening;
      a spout end defining a second opening;
      a flow passageway extending through the body from the engagement portion end to the spout end;
      at least one first recess disposed along the body between the engagement portion end and the spout end; and
      at least one second recess disposed along the body between the engagement portion end and the spout end;
   a first clamp in pivotal engagement with the body of the mandrel;
   a second clamp in pivotal engagement with the body of the mandrel wherein each of the first clamp and the second clamp comprises an inside face, an opposing outer face, and at least one tooth extending inward from the inside face; and
   a lock ring positioned for rotation about the mandrel, for rotation about the first clamp and for rotation about the second clamp, wherein rotation of the lock ring effectuates pivoting of each of the first clamp and the second clamp between an open position and a closed position;
   wherein in the closed position, the inside face of each of the first clamp and the second clamp presses against the body of the mandrel, the at least one tooth of the first clamp engages the at least one first recess, and the at least one tooth of the second clamp engages the at least one second recess to retain a storage bag to the body by pinching the storage bag between the first clamp and the body and between the second clamp and the body of the mandrel.

2. The breast milk storage system of claim 1, wherein the lock ring comprises:
   a ring portion comprising an inner surface and opposing outer surface;
   a first cam disposed along the inner surface and extending inwardly therefrom, the first cam configured to force the first clamp into the closed position upon rotation of the lock ring; and
   a second cam disposed along the inner surface and extending inwardly therefrom, the second cam configured to force the second clamp into the closed position upon rotation of the lock ring.

3. The breast milk storage system of claim 1, further comprising: a biasing mechanism that biases the first clamp into its open position.

4. The breast milk storage system of claim 3, wherein the lock ring comprises at least one cam for overcoming a force imparted on the first clamp by the biasing mechanism, thereby forcing the first clamp into its closed position upon rotation of the lock ring.

5. The breast milk storage system of claim 1, wherein the engagement portion end has a first width, the spout end has a second width less than the first width and wherein the body is tapered from the first width to the second width.

6. The breast milk storage system of claim 5, further comprising an adaptor for allowing engagement of the engagement portion end of the mandrel with the bottle connector of the breast pump.

7. The breast milk storage system of claim 5, wherein said mandrel further comprises:
   a first wing disposed along a first side of the body adjacent the spout end and extending radially out from the body; and
   a second wing disposed along a second side of the body opposite the first and adjacent the spout end and extending radially out from the body.

8. The breast milk storage system of claim 1, wherein each of the first clamp and the second clamp comprises:
   an upper flange and a lower flange, and wherein said lock ring is positioned between said upper and lower flanges.

9. A breast milk storage system comprising:
   a mandrel comprising a body and an engagement portion positioned along one end of the body for selective engagement of the mandrel with a bottle connector of a breast pump;
   a first clamp pivotally coupled to the mandrel along an outer surface of the body;
   a second clamp pivotally coupled to the mandrel along the outer surface of the body;

a lock ring comprising:
  a ring-shaped body comprising an inner surface and an opposing outer surface;
  a first cam disposed along the inner surface and extending inwardly therefrom, the first cam configured to contact the first clamp to adjust the first clamp from a first open position to a first closed position; and
  a second cam disposed along the inner surface and extending inwardly therefrom, the second cam configured to contact the second clamp to adjust the second clamp from a second open position to a second closed position,
  wherein the lock ring is rotatable about the engagement portion of the mandrel, rotatable about the first clamp, and rotatable about the second clamp.

10. The system of claim 9, wherein each of the first clamp and the second clamp comprises:
  an inner surface;
  an opposing outer surface;
  an axle defining a pivot axis for the respective first clamp or second clamp;
  a paddle comprising at least one tooth extending from the inner surface of the respective first clamp or second clamp
  wherein the mandrel further comprises at least one first recess and at least one second recess, and wherein each of said at least one first recess is sized and positioned to receive a corresponding one of the at least one tooth of the first clamp when the first clamp is in the first closed position and the at least one second recess is sized and positioned to receive a corresponding one of the at least one tooth of the second clamp when the second clamp is in the second closed position.

11. The breast milk storage system of claim 10, wherein each of the first clamp and the second clamp comprises:
  an upper flange disposed along the outer surface of the respective first clamp or second clamp and a lower flange disposed along the outer surface of the respective first clamp or second clamp, and wherein the respective first cam or second cam of the lock ring contacts the respective first clamp or second clamp between the upper flange of the respective first clamp or second clamp and the lower flange of the respective first clamp or second clamp.

12. The breast milk storage system of claim 9, wherein each of the first clamp and the second clamp comprises:
  an axle defining a pivot axis; and
  a paddle comprising an inner surface, an opposing outer surface, and a rib extending inwardly from the inner surface of the paddle of the respective first clamp or second clamp;
  wherein in the first closed position, the rib of the first clamp presses against the body and in the second closed position, the rib of the second clamp presses against the body.

13. The breast milk storage system of claim 12, wherein the rib of the paddle of the respective first clamp or second clamp is composed of a soft, compressible material.

14. The breast milk storage system of claim 9, wherein the mandrel further comprises:
  a spout disposed along an opposing second end of the body; and
  a flow passageway extending through the body from the engagement portion to the spout.

15. The breast milk storage system of claim 14, wherein said mandrel further comprises:
  a first wing proximate the spout and extending radially outward from the spout in a first direction; and
  a second wing proximate the spout and extending radially outward from the spout in a second direction opposite the first direction.

16. The breast milk storage system of claim 9, further comprising an adaptor removably coupled to the engagement portion of the mandrel.

* * * * *